United States Patent
Ford

[11] Patent Number: 5,885,246
[45] Date of Patent: *Mar. 23, 1999

[54] BREAST PUMP INSERT

[75] Inventor: Donald Robert Ford, Kedington, England

[73] Assignee: Cannon Rubber Limited, England

[*] Notice: This patent issued on a continued prosecution application filed under 37 CFR 1.53(d), and is subject to the twenty year patent term provisions of 35 U.S.C. 154(a)(2).

[21] Appl. No.: 601,712

[22] Filed: Feb. 15, 1996

[30] Foreign Application Priority Data

Feb. 16, 1995 [GB] United Kingdom .................... 9502995

[51] Int. Cl.$^6$ ....................................................... A61M 1/06
[52] U.S. Cl. ................................................. 604/74; 604/75
[58] Field of Search ................................. 604/74, 73, 75, 604/76, 35, 36, 132, 133, 346

[56] References Cited

U.S. PATENT DOCUMENTS

| | | |
|---|---|---|
| 1,690,327 | 11/1928 | Dinesen . |
| 2,670,709 | 3/1954 | Stampen . |
| 3,782,385 | 1/1974 | Loyd . |
| 4,263,912 | 4/1981 | Adams . |
| 4,680,028 | 7/1987 | Stuart . |
| 4,772,262 | 9/1988 | Grant et al. . |
| 4,794,915 | 1/1989 | Larsson ..................................... 604/74 |
| 4,799,922 | 1/1989 | Beer et al. ................................ 604/74 |
| 5,049,126 | 9/1991 | Larsson ..................................... 604/74 |
| 5,100,406 | 3/1992 | Panchula ................................... 604/74 |

FOREIGN PATENT DOCUMENTS

| | | |
|---|---|---|
| 968660 | 6/1975 | Canada . |
| 0237474 | 12/1991 | European Pat. Off. . |
| 381124 | 9/1923 | Germany . |
| 1161118 | 8/1969 | United Kingdom . |

*Primary Examiner*—Ronald Stright, Jr.
*Assistant Examiner*—A. T. Nguyen
*Attorney, Agent, or Firm*—Sofer & Haroun, LLP

[57] ABSTRACT

A flexible resilient breast pump insert (5) adapted to fit into the rigid funnel portion (1) of a vacuum generating breast pump operable to generate a negative pressure. The insert comprises a mouth portion (6) with an open end shaped to receive and contact the areola of a woman's breast and an inner portion (7) of reduced size to receive the woman's nipple. A lip (9) around the edge of the mouth portion allows it to be connected to the rigid breast pump funnel portion (1) to form a pressure tight seal therewith. The mouth portion (6) of the insert has a wall with an inner surface (6b) shaped to contact the woman's areola around her nipple and an outer surface (6a) with a plurality of recesses (10) formed in it, the thickness of the wall of the mouth portion in the region of each recess (10) being less than that of the remainder of the mouth portion and each recess (10) having a channel (12) leading from it to connect it with a source of negative pressure so that, in use, each recess (10) can be deformed and deflected into contact with the inner surface of the rigid funnel portion of the breast pump in response to a negative pressure applied to the outer surface of the wall of said mouth portion (6) thereby massaging the areola region of the breast and stimulating the lactation of milk from the nipple.

23 Claims, 3 Drawing Sheets

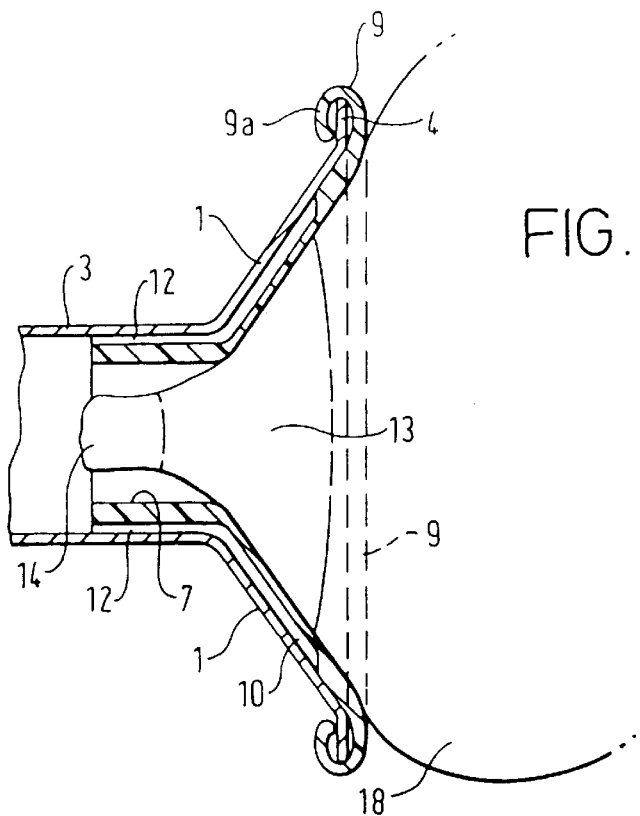
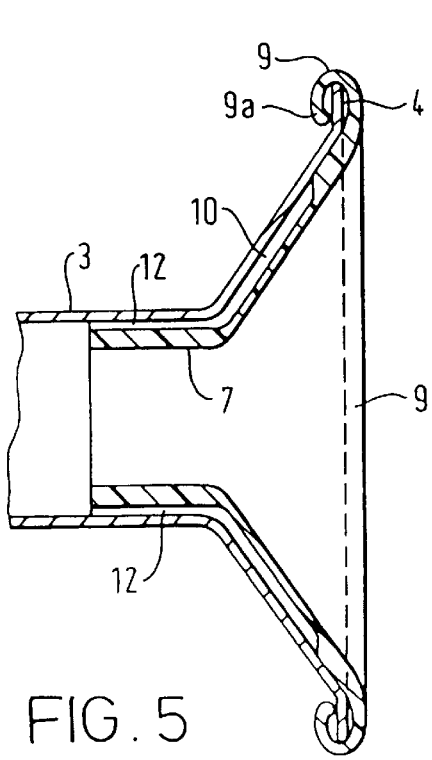
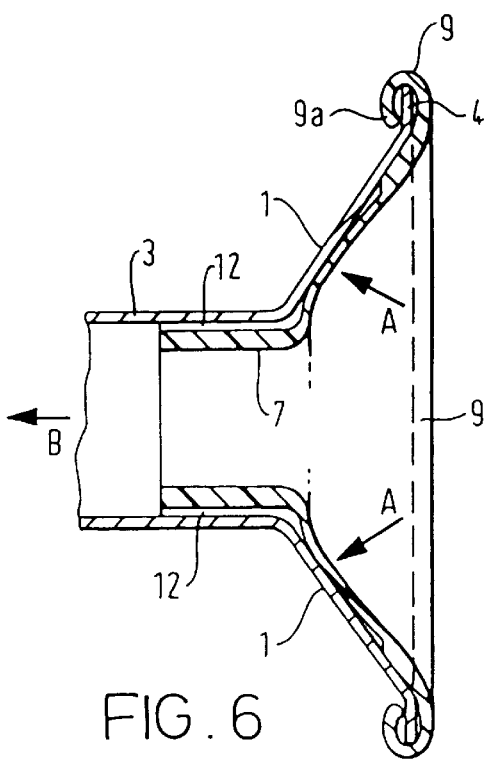

BREAST PUMP INSERT

This invention relates to a flexible resilient breast pump insert which is adapted to fit into the rigid funnel portion of a vacuum generating breast pump.

Most existing breast pumps only apply a negative pressure to the end of a mother's nipple so they do not directly stimulate the nerve endings in the areola of the breast. During lactation, the effective removal of the milk from the breast happens as a result of the milking action provided by the baby's mouth and jaw movements once the "let down" reflex is activated due to the mother's "oxytocin" release.

It is therefore an object of the present invention to provide an insert for use with a breast pump which is specifically designed to stimulate the areola region around the nipple rather than the nipple itself when a negative pressure is applied to the mother's breast when in position in the insert.

According to one aspect of the invention there is provided a flexible resilient insert adapted to fit into the rigid funnel portion of a vacuum generating breast pump operable to generate a negative pressure, the insert comprising a mouth portion having an open end shaped to receive and contact the areola of a woman's breast and an inner portion of reduced size to receive the woman's nipple, connection means around the mouth portion for connecting said mouth portion to the rigid breast pump funnel portion to form a pressure tight seal therewith, the mouth portion having a wall with an inner surface adapted to contact the woman's areola around the nipple and an outer surface with at least one recess formed therein, the thickness of the mouth portion wall in the region of the or each recess being less than that of the remainder of the mouth portion and means operable to connect the or each recess with the source of negative pressure whereby, in use, the or each region of reduced wall thickness is deformed and deflected into contact with the inner surface of the rigid funnel portion of the breast pump in response to a negative pressure applied to the outer surface of the wall of said mouth portion thereby massaging the areola region of the breast and stimulating lactation of milk from the breast.

Preferably the inner portion of the mouth piece is of a size such that the walls thereof do not contact the wearer's nipple. In the preferred embodiment, the inner portion is tubular and open ended.

Preferably a plurality of discrete recesses or pockets are provided around the flexible mouth portion so that they are positioned to surround the areola. Ideally, the recesses or pockets are equidistantly circumferentially spaced from each other. However, an annular recess could be used.

In the preferred embodiment, the connection means on the flexible mouth portion comprises an annular lip adapted to fit over and engage with the outer edge of the rigid funnel of the breast pump. Conveniently the annular lip is molded to provide an undercut or rebate which engages with a flange extending outwardly from the edge of the rigid breast pump funnel.

When the insert has several recesses or pockets in it, each recess is preferably pear-shaped when viewed in plan, the major axis thereof being aligned with the main axis of the insert.

Preferably, the or each recess is connected by duct means to the source of negative pressure so that the negative pressure acts on the outer surface of the wall of the flexible mouth portion.

Conveniently, the duct means connecting each recess with the source of negative pressure is a conduit formed in the outer surface of the tubular inner portion, said conduit leading from each recess to the remote end of said inner tubular portion. Preferably each conduit is an open channel formed in the outer wall surface of the inner tubular portion and extends from the narrow end of the recess to the end face of the inner tubular portion.

In a preferred embodiment, a continuous upstanding annular bead extends between each conduit and along each side thereof and around each recess which is operable, in use, to form a vacuum tight seal with the inner surface of the funnel when a negative pressure is applied to the conduits and recesses.

Preferably the flexible insert is molded in one-piece from natural or synthetic rubber material or latex. Silicone rubber is the preferred material although any elastomer could be used.

According to another aspect of the invention, there is provided a flexible resilient insert adapted to fit into the rigid funnel portion of a breast pump, the insert comprising a mouth portion having an open end shaped to receive and contact the areola of a woman's breast and an inner portion of reduced size to receive the woman's nipple, connection means around the mouth portion for connecting said mouth portion to the rigid breast pump funnel portion to form a pressure tight seal therewith, the mouth portion having a wall with an inner surface adapted to contact the woman's areola around the nipple and an outer surface with at least one recess formed therein, the thickness of the mouth portion wall in the region of the or each recess being less than that of the remainder of the mouth portion and means connecting the or each recess with a source of positive pressure whereby the or each region of reduced wall thickness can be inflated and deformed and deflected into contact with a woman's breast thereby massaging the areola region of the breast and stimulating lactation of milk from the breast.

Preferred embodiments of the invention will now be described, by way of example only, with reference to the accompanying drawings in which:

FIG. 4 is a diagrammatic cross section showing a flexible insert of the present invention inserted in a rigid breast pump funnel with a woman's breast in position in said insert;

FIG. 5 is a view similar to FIG. 4 but omitting the woman's breast and showing the insert in its relaxed condition; and FIG. 6 is a view similar to FIG. 5 but showing the insert in its distorted condition with parts of the wall of the mouth portion contacting the inner surface of the rigid breast pump funnel;

Figure 1:
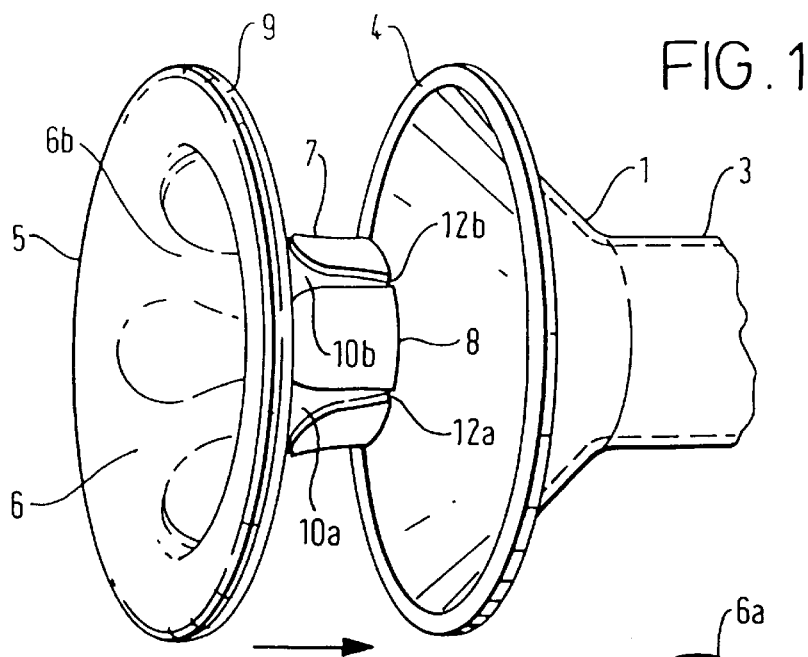
FIG. 1 is a perspective view showing a flexible insert of the present invention prior to insertion into the rigid funnel portion of a breast pump (not shown)

Referring now to the drawings, there is shown in FIG. 1 a flexible resilient insert 5 of the present invention just prior to insertion into the rigid funnel portion 1 of a known breast pump (not shown). The rigid funnel portion 1 is conical in shape and includes an inner tubular portion 3 extending forwardly therefrom connected to the breast pump body (not shown). The rigid funnel portion 1 has an outwardly extending flange 4 around its circumference for reasons which will be explained hereafter.

The flexible insert 5 is molded in one-piece and includes a conical mouth portion 6 which is connected to a tubular inner portion 7 whose outer diameter is substantially equal to or slightly smaller than the internal diameter of the inner tubular portion 3 of the breast pump funnel. The outer edge of the mouth portion 6 is molded with an annular bead 9 which includes a rebate 9a therein (see FIGS. 4–6) so that the flexible insert 5 can be attached to the annular bead 4 on the rigid funnel portion 1 of the breast pump to make a fluidtight seal therewith.

Figure 2:
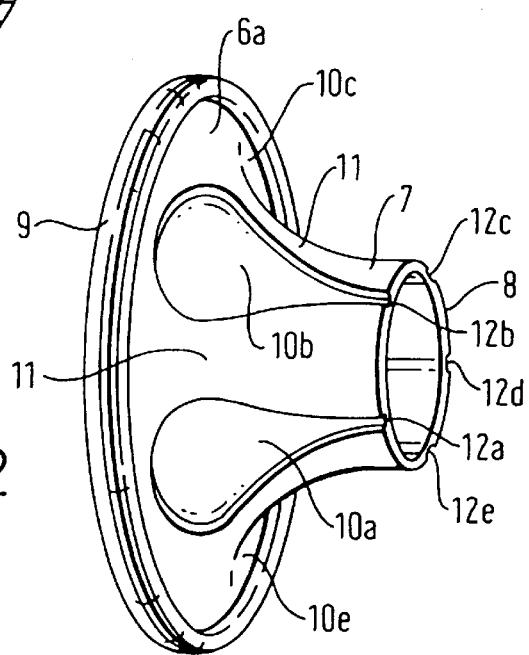
FIG. 2 is a perspective view of the flexible insert shown in FIG. 1 but illustrating the rear face thereof.
Figure 3:
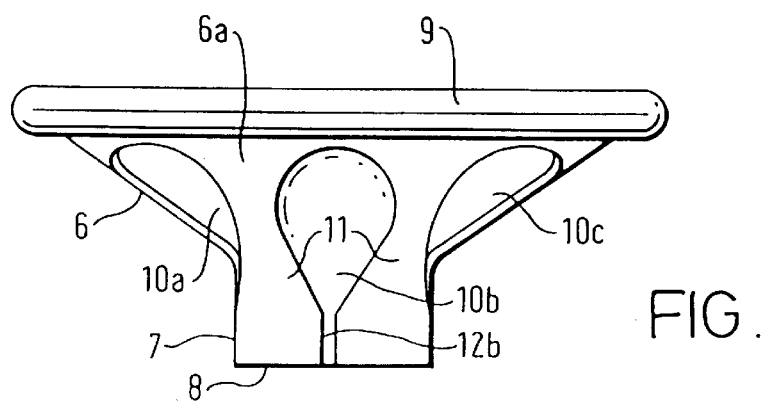
FIG. 3 is a top view of the flexible insert shown in FIGS. 1 and 2.

The inner surface 6B of the mouth portion 6 is smooth as is the inner surface of the tubular inner portion 7. However, the outer surface 6A (see FIGS. 2 and 3) of the mouth portion 6 is formed with recesses or pockets 10a–10e which are preferably pear-shaped as illustrated and extend partially along the inner tubular portion 7. A duct, conduit or channel 12 is molded into the outer surface of the inner tubular portion 7 and extends from the tapered end of each recess 10 to end face 8 of the inner tubular portion 7 for reasons to be explained hereafter. Five recesses or pockets 10a–10e are shown in the illustrated embodiment which are arranged circumferentially around the flexible mouth portion 6 and spaced apart by equal amounts to leave thicker fingers 11 therebetween. It will be appreciated that the thickness of the mouth portion 6 in the region of the finger portions 11 is the full thickness of the mouth portion wall whereas in the pocket regions 10, the bottom wall of each pocket is of a reduced thickness. This can be better seen in the cross sectional views of FIGS. 4–6. Thus, the finger portions 11 provide harder portions around the mouth portion which in use, act on and stimulate the breast. Although five pockets 10 are illustrated, it will be appreciated that the number and configuration of the pockets is not critical. For instance, an annular pocket could be formed in the mouth portion 6.

Figure 7:
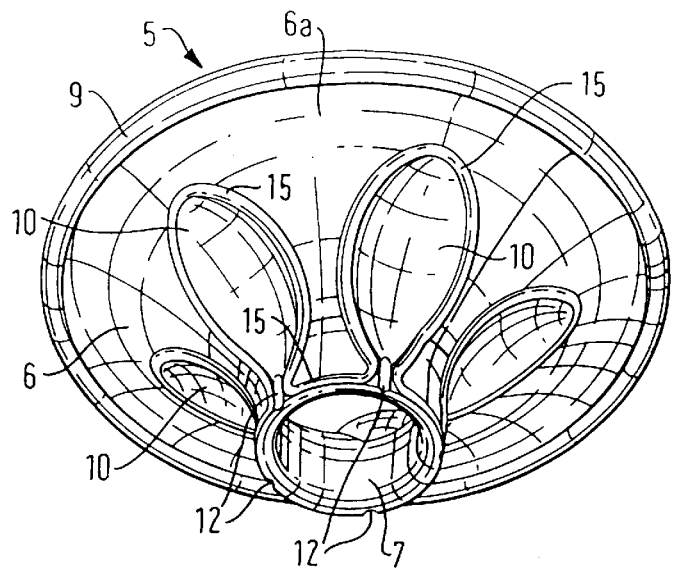
FIG. 7 is an underneath perspective view of a modified insert which includes an annular sealing bead and differently configured recesses.

The modified insert shown in FIG. 7 is very similar to that just described except that it includes an upstanding annular bead 15 extending between and alongside each channel 12 and around each recess 10. In use, this bead is deflected into contact with the inner surface of the funnel (not shown) to form a fluidtight seal therewith when a negative pressure is applied to the recesses 10 as has already been described. As a result, any leakage of vacuum from the recess 10 is reduced so the users breast is more positively stimulated.

Figure 8:
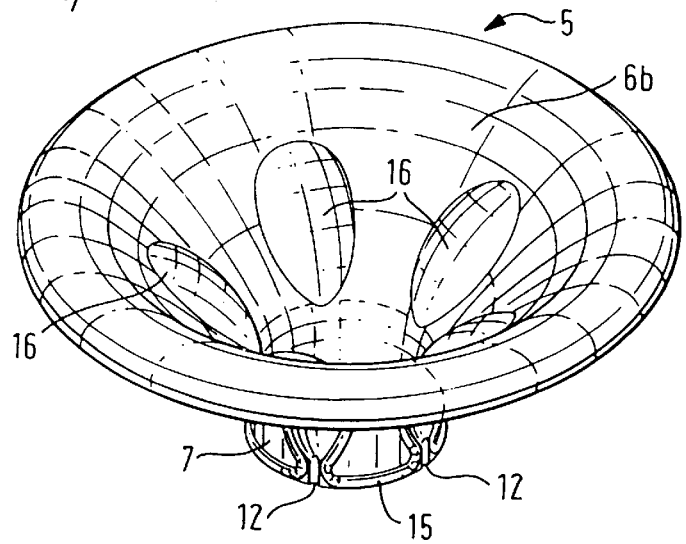
FIG. 8 is a top perspective view of the insert shown in FIG. 7.
Figure 9:
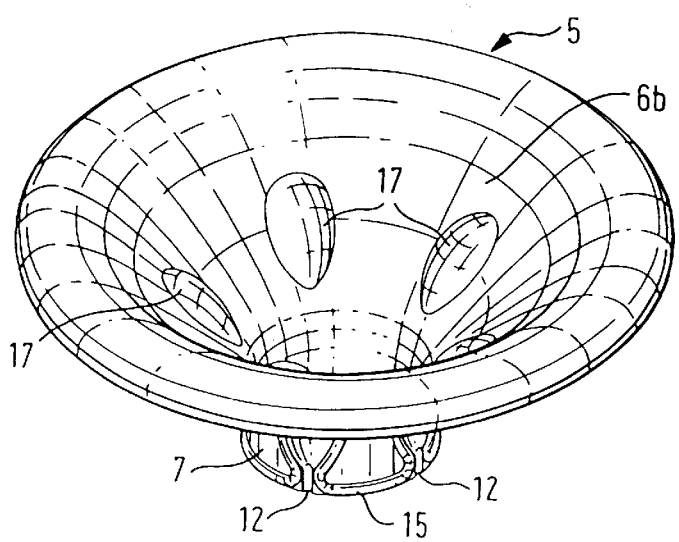
FIG. 9 is a top perspective view of a still further modified insert with protrusions molded on the inner surface thereof.

To further improve this stimulation effect, the inner surface 6b of the insert can have inwardly extending protrusions formed thereon which are operable to apply local pressure to the user's breast. These can be formed by making the bottom of each recess 10 arcuate so that it protrudes inwardly of the inner surface 6b to provide the arcuate configurations 16 shown in FIGS. 7 and 8. Alternatively, the bottom of each recess can be planar and each protrusion can be formed as a solid lump 17 which protrudes from the inner surface 6b as shown in FIG. 9.

The main purpose of the present invention is to provide stimulating means on the insert which contact the areola region only and are operable to stimulate the areola to encourage lactation.

In use, the flexible insert 5 is attached to the rigid breast pump funnel portion 1 by engaging the annular lip 9 over the annular flange 4 to form an airtight seal therewith. The outer diameter of the inner tubular portion 7 of the flexible insert 5 is preferably slightly less than the inner diameter of the tubular portion 3 of the rigid funnel portion 1 of the breast pump although it can be of substantially the same diameter if necessary.

When the insert 5 is properly attached to the rigid breast pump funnel portion 1, it assumes the position shown in FIGS. 4–6. FIG. 4 shows the position of the mother's breast 18 when inserted in the insert 5 and it can be seen that the breast tissue fills the mouth portion 6. It will be noted however that only the areola is in contact with the inner surface of the conical mouth portion 6, the nipple 14 protruding into the tubular inner portion 7 but not in contact with the inner walls thereof. This is intentional as the insert 5 of the present invention is designed to manipulate only the areola portion of the breast 18 rather than the nipple to encourage lactation in a manner to be described shortly.

When a negative pressure is generated by the breast pump (not shown) in known manner, this causes the pockets 10 to collapse and be sucked outwardly into contact with the inner surface of the conical portion 2 of the rigid funnel portion 1 of the breast pump, the space in the pockets communicating with the source of negative pressure by means of the channels 12. On release of the negative pressure, the pockets 10 return to their original configuration and thereby apply a pressure to the areola 13 on the breast 18 to encourage lactation. In the FIGS. 7–9 embodiments, it is the bead 15 which makes the seal with the funnel (not shown) and lactation is further encouraged by the additional stimulation applied to the user's breast by the protrusions 16 or 17. The harder finger portions 11 between the pockets 10 also distort and move thereby providing an additional massaging action to the breast. This process repeats on a cyclic basis to stimulate milk flow from the mother's breast 18 when connected to the vacuum pump (not shown).

It will be appreciated from the foregoing description of the illustrated preferred embodiments that the flexible insert has the following features:

a) a hollow mouth piece 6 with a large opening at one end to accept the mother's breast, b) the mouth portion 6 reduces in size to a smaller tubular section 7 which accepts only the breast nipple, c) the undercut 9a on the annular bead 9 of the mouth portion 6 attached and seals the insert 5 onto the rigid funnel portion 1 of the vacuum pump in a simple and effective way, d) the outside surface of the insert 5 is substantially the same shape as that of the inner surface of the rigid funnel portion 2 so it fits readily therein, e) the mouth portion 6 of the flexible insert 5 has a number of recesses or "air cells" 10 connected annularly by the thicker finger sections 11 which support the flexible mouth portion 6 in the rigid funnel 1 of the vacuum pump, f) each air cell 10 is located in an area of the mouth portion 6 such that it is positioned in the areola part of the mother's breast and it is connected to the vacuum chamber of the breast pump by means of the small vents or ducts 12 provided around the tubular inner section 7, g) when the flexible insert 5 is in position on the vacuum pump funnel 1 and the mother's breast is in place within it, the cyclic action of the negative pressure from the pump enables the air cells 10 to collapse against the rigid funnel 1. This dynamic movement of the air cells 10 in conjunction with that of the thick finger sections 11 around the areola in the direction of arrow A (see FIG. 6) stimulates the breast in a manner which provides a finger type pressure on the milk ducts thereby squeezing the milk therefrom. If necessary, one or more holes (not shown) can be provided in the pockets 10 to allow milk removed from the breast to pass through the pockets, into the space between the insert 5 and the inner surface of the rigid funnel 1 and thereafter to flow over the outer surface of the tubular inner portion 7 and into the milk collecting container attached to the breast pump (neither of which is shown) in the direction of arrow B (see FIG. 6).

It is also envisaged within the scope of the invention that the ducts 12 could be omitted. This would mean that pockets of air would be trapped in the recesses 10a–10e between the flexible insert 5 and the rigid funnel portion 1. When the negative pressure generated by the breast pump acts on the nipple, the breast will be pulled towards the recesses 10 and, as a result, the harder finger portions 11 will press against the breast and encourage lactation.

I claim:

1. A flexible resilient insert for use with a rigid funnel portion of a breast pump operable to generate a negative pressure, the insert comprising:

a conical mouth portion shaped to fit into the rigid funnel portion of the pump and receive a woman's breast, the conical mouth portion having an inner wall with at least one recess formed therein; and attachment means mounted on the conical mouth portion for sealingly attaching the insert to the rigid funnel portion of the breast pump so that, in use, each recess can be deformed in a direction away from a woman's breast towards the rigid funnel portion in response to the negative pressure generated between the conical mouth portion of the insert and the rigid funnel portion of the pump.

2. An insert as claimed in claim 1, further comprising a second recess formed with the conical mouth portion, wherein the recesses comprise a plurality of discrete pockets positioned circumferentially around the conical mouth portion.

3. An insert as claimed in claim 2, wherein each recess is formed in the shape of a petal.

4. An insert as claimed in claim 1, wherein the rigid funnel has an outer edge and the attachment means is provided with an annular lip shaped to fit over and sealingly engage with said outer edge of the rigid funnel of the breast pump.

5. An insert as claimed in claim 4, wherein said annular lip is molded to provide an undercut which sealingly engages said outer edge.

6. An insert as claimed in claim 1, wherein the conical mouth portion of the insert has an inner portion of reduced size with an outer surface and a remote end, wherein a conduit is formed in said inner portion to place each recess in communication with the source of negative pressure generated by the pump.

7. An insert as claimed in claim 6, wherein each conduit is an open channel formed in the outer surface of the inner portion of the insert.

8. An insert as claimed in claim 7, wherein a continuous upstanding bead extends along both sides of each channel and around each recess, so that, in use, said bead can form a fluid tight seal with the rigid funnel of the breast pump.

9. An insert as claimed in claim 1, wherein the conical mouth portion thereof has an inner frusto conical surface which, in use, receives the woman's breast, each recess having a bottom wall which is arcuate and protrudes inwardly from said inner frusto conical surface.

10. An insert as claimed in claim 1, wherein the insert is molded from a synthetic rubber material.

11. An insert as claimed in claim 1, wherein the insert is molded from a silicone material.

12. A flexible resilient insert for use with a rigid funnel portion of a breast pump operable to generate a negative pressure, the insert comprising:

a conical mouth portion shaped to fit into the rigid funnel portion of the pump and receive a woman's breast, the conical mouth portion having an inner and outer surface, at least one recess formed in said outer surfaces having a wall portion which is deformable in a direction towards said outer surface when a negative pressure produced by the pump is applied to the exterior surface of the conical mouth portion; and attachment means mounted on the conical mouth portion for sealingly attaching the insert to the rigid funnel portion of the breast pump so that, in use, the or each recess can be deformed in a direction away from the woman's breast and towards the rigid funnel portion in response to the negative pressure generated between the conical mouth portion of the insert and the rigid funnel portion of the pump.

13. An insert as claimed in claim 12, further comprising more than one recess formed in the conical mouth portion, wherein the recesses comprise a plurality of discrete pockets positioned circumferentially around the conical mouth portion.

14. An insert as claimed in claim 13, wherein each recess is formed in the shape of a petal.

15. An insert as claimed in claim 12, wherein the rigid funnel has an outer edge and the attachment means is provided with an annular lip shaped to fit over and sealingly engage with said outer edge of the rigid funnel of the breast pump.

16. An insert as claimed in claim 15, wherein said annular lip is molded to provide an undercut which sealingly engages said outer edge.

17. An insert as claimed in claim 12, wherein the conical mouth portion of the insert has an inner portion of reduced size with an outer surface and a remote end, wherein a conduit is formed in said outer surface of said inner portion to place the recess in communication with the source of negative pressure generated by the pump.

18. An insert as claimed in claim 17, wherein the conduit is an open channel formed in the outer surface of the inner portion of the insert.

19. An insert as claimed in claim 18, wherein a plurality of recesses are formed in the conical portion and a continuous upstanding bead extends along both sides of each channel and around each recess, so that, in use, said bead can form a fluid tight seal with the rigid funnel of the breast pump.

20. An insert as claimed in claim 12, wherein the conical mouth portion thereof has an inner frusto conical surface which, in use, receives the woman's breast, each recess having a bottom wall which is arcuate and protrudes inwardly from said inner frusto conical surface.

21. An insert as claimed in claim 12, wherein the insert is molded from a synthetic rubber material.

22. An insert as claimed in claim 12, wherein the insert is molded from a silicone material.

23. A flexible resilient insert for insertion into a rigid conical funnel portion of a breast pump operable to cyclicly generate and release a negative pressure, the insert comprising a conical mouth portion shaped to fit into the rigid funnel portion of the pump and receive a woman's breast therein, the conical mouth portion having an inner surface and an outer surface, a plurality of pockets formed in said outer surface, each pocket having a projecting portion which protrudes from the inner surface of the conical mouth portion to normally contact the woman's breast but being deformable outwardly in a direction away from the woman's breast on the application of a negative pressure to the outside surface of the insert, the projecting portions returning to their original configurations on release of the negative pressure.

* * * * *